United States Patent [19]

Sauer et al.

[11] Patent Number: 5,496,341

[45] Date of Patent: Mar. 5, 1996

[54] SURGICAL DEVICE TO PREPARE BODY TISSUE FOR ANASTOMOSIS

[75] Inventors: Jude S. Sauer, Pittsford; Theodore J. Tiberio, Hilton; Roger J. Greenwald, Holley, all of N.Y.

[73] Assignee: Lasersurge, Inc., Rochester, N.Y.

[21] Appl. No.: 296,873

[22] Filed: Aug. 26, 1994

Related U.S. Application Data

[63] Continuation of Ser. No. 957,601, Oct. 6, 1992, abandoned.

[51] Int. Cl.⁶ ............................ A61B 17/125; A61B 17/32
[52] U.S. Cl. ............................ 606/167; 606/171; 606/207
[58] Field of Search ............................ 606/167, 181–183, 606/135, 174, 175, 151, 157, 158; 128/843

[56] References Cited

U.S. PATENT DOCUMENTS

| | | |
|---|---|---|
| 352,245 | 11/1886 | Hullhorst . |
| 640,517 | 1/1900 | Acheson . |
| 821,183 | 5/1906 | Nettleton . |
| 848,126 | 3/1907 | Roosevelt . |
| 1,854,582 | 4/1932 | Erichsen . |
| 1,918,700 | 7/1933 | Harris ............................ 606/174 |
| 1,982,207 | 11/1934 | Furniss . |
| 2,646,799 | 7/1953 | Jacoby, Jr. ............................ 606/181 |
| 2,930,376 | 3/1960 | Rathmann ............................ 606/174 |
| 2,932,296 | 4/1960 | Sanders . |
| 3,006,344 | 10/1961 | Vogelfanger . |
| 3,019,789 | 2/1962 | Whitehill et al. . |
| 3,175,556 | 3/1966 | Wood et al. . |
| 3,287,751 | 11/1966 | Hoffman . |
| 3,451,396 | 6/1969 | Collins ............................ 606/167 |
| 3,492,994 | 2/1970 | Field . |
| 3,631,858 | 1/1972 | Ersek . |
| 3,683,925 | 8/1972 | Frankel . |
| 3,716,056 | 2/1973 | Brodsky et al. . |
| 4,286,598 | 9/1981 | Kapitanov et al. . |
| 4,428,374 | 1/1984 | Auburn . |
| 4,569,346 | 2/1986 | Poirier . |
| 4,602,629 | 7/1986 | Schnirman . |
| 4,682,598 | 7/1987 | Beraha ............................ 128/843 |
| 4,716,886 | 1/1988 | Schulman et al. . |
| 4,807,622 | 2/1989 | Ohkaka et al. . |
| 4,817,602 | 4/1989 | Beraha . |
| 4,872,455 | 10/1989 | Pinchuk et al. . |
| 5,009,657 | 4/1991 | Cotey et al. . |

FOREIGN PATENT DOCUMENTS

| | | |
|---|---|---|
| 0134750 | 3/1985 | European Pat. Off. . |
| 2561904 | 10/1985 | France . |
| 3322741 | 1/1985 | Germany . |

Primary Examiner—Tamara L. Graysay

[57] ABSTRACT

The present invention provides a surgical device which atraumatically compresses body tissue and guides a cutting blade to transect the body tissue. Included in the surgical device is a base member equipped to hold body tissue and accurately guide a cutting blade to sever tissue at a predetermined location. A pressure applying member, preferably an arm pivotally connected to the base member, atraumatically compresses a portion of the body tissue through a compliant finger projecting from its distal end. The complaint finger is configured and dimensioned to engage the holding portion of the base member, preferably a groove formed within the base member. Parallel guiding members intersect the holding portion of the base member to guide a cutting blade substantially perpendicular to the body tissue during tissue severance.

21 Claims, 5 Drawing Sheets

SURGICAL DEVICE TO PREPARE BODY TISSUE FOR ANASTOMOSIS

This is a continuation of application Ser. No. 07/957,601 filed on Oct. 5, 1992, now abandoned.

BACKGROUND OF THE INVENTION

1. Field of the Invention

The present invention relates to surgical devices for holding tissue to be cut and, more particularly, to a device for providing compression to a portion of body tissue and for providing guidance for a cutting blade to cut the body tissue.

2. Brief Description of the Related Art

Anastomotic procedures are well known in the surgical arts. As used herein, anastomosis is any surgical procedure which unites parts or branches of vessels, organs, or other tissue structures, such as nerves and tendons, such that the vessels, organs or tissue structures communicate by collateral channels. Typically, tissue is cut on either side of a pathologic segment to facilitate removal of the segment. Successful reconnection of the remaining tissue portions depends upon the shape and condition of the severed ends remaining in the patient. To optimize tissue for most types of reconnections, the severed tissue ends remaining in the patient should be cleanly and consistently transected. The inner layers of the tissue should not bulge or protrude toward the anastomotic line relative to the outer layers, i.e., the layers of the severed tissue ends must be flush.

Prior art surgical cutting devices fail to provide severed tissue ends of the quality needed for subsequent anastomosis. Conventional instruments such as scalpels, razors, scissors, and the like, transect tissue without differential compression along the tissue section length during cutting. Without such differential compression, the severed tissue ends tend to display bulging of their inner contents, forming unsatisfactory hemispherical end profiles.

Current instruments for preparing tissue structures for subsequent anastomosis fail to cut the structures under the necessary differential compression for optimal tissue end profiles. For example, U.S. Pat. No. 4,872,455 to Pinchuk et al. describes a device for trimming a tubular structure to mate with a similarly trimmed end of a second tubular structure. The device comprises a pair of pivotally-connected arms, one of which carries a cutting element and the other of which carries a V-shaped notch. A tubular structure sits in the notch as the arms are approximated, cutting the tubular structure. No element of the Pinchuk device compresses the tubular tissue prior to or during the cutting stroke, thus no differential compression is provided.

A need in the art therefore exists for a surgical device which applies differential compression along the length of a tissue structure while providing guidance for a cutting blade to transect the structure. Such a device would permit the user to safely and easily prepare vessels, organs, and other tissue structures for subsequent anastomosis by providing severed tissue end profiles having flush inner and outer layers.

SUMMARY OF THE INVENTION

The present invention provides a surgical device for preparing body tissue for anastomosis. The device atraumatically compresses body tissue and guides a cutting blade to transect the body tissue. Included in the surgical device is a base member equipped to hold the body tissue and accurately guide a cutting blade to sever tissue at a predetermined location. A pressure applying member, preferably an arm pivotally connected to the base member, atraumatically compresses a portion of the body tissue through a compliant finger projecting from its distal end. The compliant finger is configured and dimensioned to engage the holding portion of the base member, preferably a groove formed within the base member.

To guide a cutting blade for tissue transection, guiding elements are formed in the base member. Preferably, the guiding elements take the form of parallel grooves which intersect the holding portion of the base member on either side of the region cooperating with the pressure-applying compliant finger. The grooves guide a cutting blade, e.g., a scalpel or razor blade, such that the blade is substantially perpendicular to the body tissue during tissue severance.

The present invention also provides a method for preparing body tissue for subsequent anastomosis using the novel surgical device. In this method, tissue is provided with two severed ends using the above-described surgical device, the portion between the severed ends being removed. The severed ends are subsequently anastomosed by conventional surgical procedures.

BRIEF DESCRIPTION OF THE DRAWINGS

FIG. 6A shows a vas deferens to be cut using the instrument of the present invention;

FIG. 6B shows the vas inserted into the instrument;

FIG. 6C shows the instrument being closed to compress a portion of the vas;

FIG. 6D shows a scalpel blade inserted into the instrument to transect the vas;

FIG. 6E shows the vas deferens following transection and anastomosis.

DETAILED DESCRIPTION OF THE PREFERRED EMBODIMENTS

Figure 1:
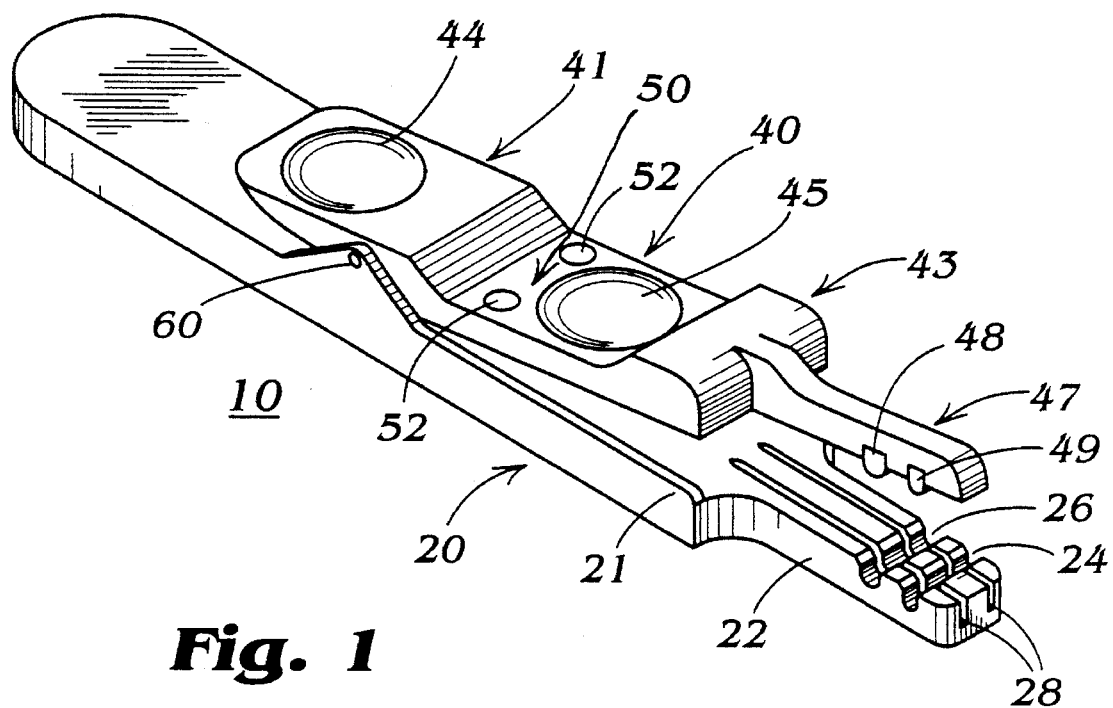
FIG. 1 is a perspective view of the surgical instrument of the present invention in an open position.
Figure 2:
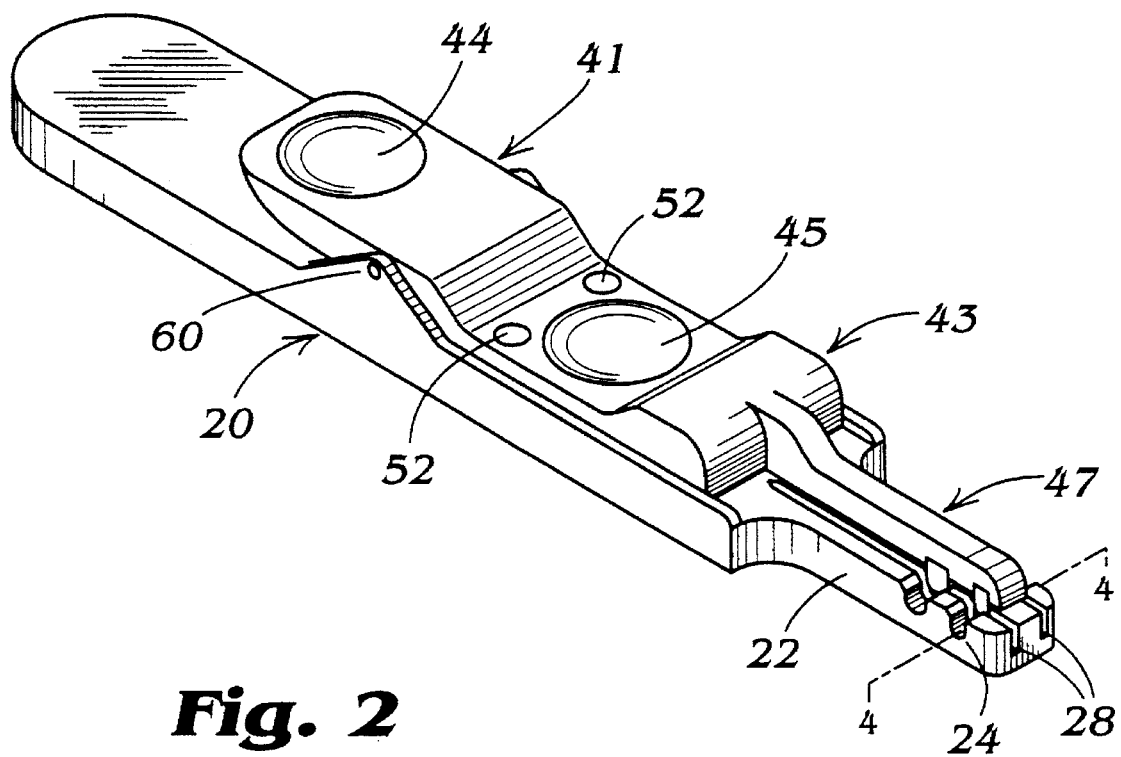
FIG. 2 is a perspective view of the instrument of the present invention in a closed position.

Referring now to the drawings in detail where like reference numerals indicate like elements in each of the several views, reference is first made to FIGS. 1 and 2 wherein a surgical device for compressing body tissue and providing cutting blade guidance 10 is depicted. The device 10 includes a base member 20 adapted to hold body tissue and guide the cutting blade and compression arm 40 pivotally mounted thereto by means of pivot pin 60. Ridge 21 provides alignment support between base member 20 and compression arm 40.

Figure 3:
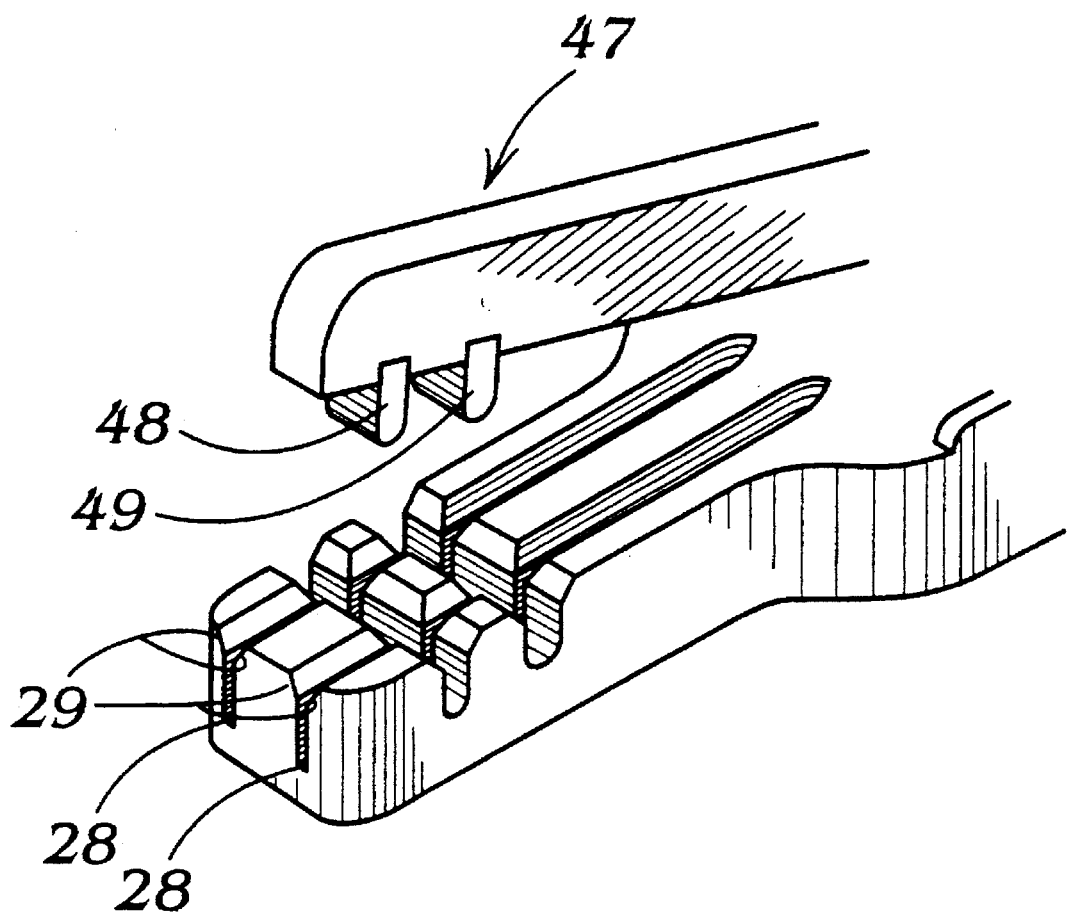
FIG. 3 is an enlarged perspective view of the distal end of the instrument of FIG. 1.
Figure 5:
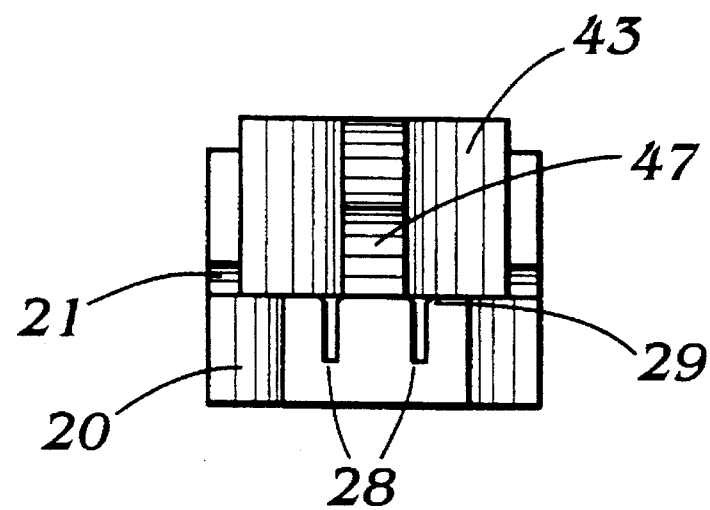
FIG. 5 is a distal end view of the instrument of FIG. 1.

Base member 20 has a flat, elongated configuration to facilitate gripping by the user. At its distal end, a working head 22 extends from the base member. This head serves as the template portion of the instrument, holding tissue to be cut in operative relation to the blade-guiding elements. Disposed in head 22 and transverse to the longitudinal axis thereof are tissue-capturing grooves 24 and 26. Grooves 24 and 26 traverse the width of working head 22 and, in a preferred embodiment, have a generally U-shaped cross-section with beveled upper edges, best seen in FIGS. 3 and 5. The shape of grooves 24 and 26 may be configured for use with the particular type of body tissue to be cut. Preferably, grooves 24 and 26 are of unequal size, making the device capable of severing a range of body tissue structures.

Parallel to the longitudinal axis of head 22 and generally perpendicular to tissue-capturing grooves 24 and 26 are grooves 28 for guiding the cutting blade used to sever the body tissue. The guiding grooves intersect the tissue-capturing grooves and orient the cutting blade so that it remains perpendicular to the tissue. At their lowermost edges, grooves 28 penetrate more deeply into head 22 than do grooves 24 and 26 (FIG. 4), assuring correct blade orientation at the point of tissue transection. In use, a standard scalpel or razor blade or the like is inserted into a groove and is drawn proximally toward and through the specimen to provide tissue transection. Upper groove edges 29 are beveled, FIGS. 3 and 5, to facilitate blade insertion into the guiding grooves. To protect the user's hand from the cutting blade, compression arm 40 includes shoulder section 43 which acts as a blade stop between scalpel grooves 28 and the user's hand.

To gently compress the body tissue held in groove 24 or 26, a pressure applying pivotal arm 40 is provided. As best seen in FIGS. 1 and 2, the arm comprises a proximal gripping section 41, shoulder section 43, and compressing head section 47. Arm 40 is pivotally mounted to base member 20 through pivot pin 60. The arm is biased to a closed position, FIG. 2, in contact with base member 20, through tensioning mechanism 50. Two urethane springs 52, attached between the arm and the base member distal to pivot pin 60, provide the appropriate arm compression on the tissue structure during transection.

Gripping section 41 includes opening finger grip 44 and closing finger grip 45. Opening finger grip 44, a generally circular-shaped depression in the proximal end of arm 40, allows the user to conveniently open the arm to position tissue in the appropriate base member groove. Closing finger grip 45, similarly shaped to grip 44 and located distally therefrom, permits application of additional holding power, if needed, during positioning of the body tissue. Note however, that tensioning mechanism 50 alone provides the appropriate compression on the tissue structure during transection. Because grip 45 is placed behind shoulder section 43, the user's finger is shielded from the working head region.

Compressing head section 47 extends distally from shoulder section 43 and includes compliant fingers 48 and 49. Fingers 48 and 49 have generally U-shaped cross sections adapted to engage grooves 26 and 24, respectively, to gently compress the body tissue held therein. As with tissue-holding grooves 24 and 26, fingers 48 and 49 can be configured for compressing a particular type of body tissue to be cut, thus a variety of shapes for the compliant fingers and tissue grooves are contemplated. Preferably, the compliant fingers are fabricated from a resilient, elastomeric material to atraumatically compress the tissue.

Figure 4:
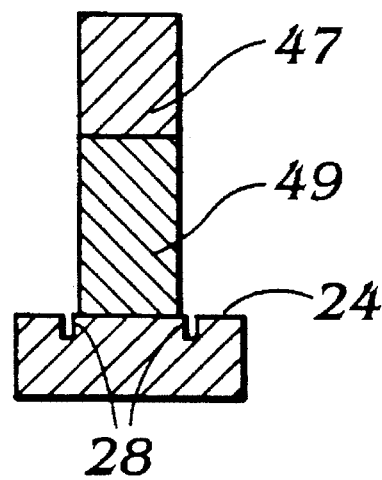
FIG. 4 is a transverse cross-section across the tissue groove at line 4—4 of FIG. 2.

As best seen in FIGS. 2 and 4, the width of head section 47 and fingers 48 and 49 is less than the width of base member working head 22 so as to provide differential compression along the length of the tissue captured in grooves 24 and 26. The width is equal to the distance between guiding grooves 28, the head being centrally disposed between and adjacent to the guiding grooves during arm closure. In this position, guiding grooves 28 intersect tissue-holding grooves 24 and 26 immediately adjacent the edge of arm 40 and fingers 48 and 49. Thus, body tissue disposed in a tissue groove is compressed in the portion of the groove beneath the finger and is uncompressed in the remaining portions of the groove on either side of the finger. This configuration provides the differential compression during tissue severance necessary to provide a surface suitable for anastomosis. Tissue ends severed by the surgical instrument have a flush profile, i.e., inner and outer tissue layer surfaces are even with one another.

OPERATION

The surgical instrument of the present invention has particular application in severing the vas deferens during a vasectomy reversal procedure (vasovasotomy) as illustrated in FIGS. 6A–6E. In this procedure, a routine technique for exposure of a vasectomy site 100 shown in FIG. 6A, through both sides of the scrotum is performed. The surgical instrument 10, held open by pressing grip 44, is slid under the vas deferens on the testicular side of the vasectomy granuloma, FIG. 6B. The vas is placed in the approximately-sized tissue holding groove, here, 26. The instrument is closed, FIG. 6C with the corresponding finger 48 gently compressing the vas held in the tissue groove. If further dissection or manipulation is necessary, the vas can be more securely held by applying pressure on closing finger grip 45.

Prior to cutting, finger pressure is released from the closing finger grip allowing tensioning mechanism 50 alone to provide the necessary tissue compression. A standard scalpel blade 120 is placed in the distal end of the blade-guiding groove adjacent the specimen side of the compliant finger. The blade is drawn toward and through the specimen to provide tissue transection, FIG. 6D. The instrument is then opened and removed.

To transect the contralateral side, the instrument is opened and placed on the abdominal (prostatic) side of the vasectomy granuloma. The vas is placed in the appropriately sized tissue groove and the instrument is closed. The same cutting technique is followed using the opposite blade-guiding groove, which should be placed adjacent to the specimen side of the tissue. The resultant tissue structures remaining in the patient, i.e., the portion cut under gentle compression, have flush anastomotic surfaces. The uncompressed sides having exaggerated bulging are discarded with the resected specimen.

Routine assessment of the vas patency and seminal sperm content are conducted. Further vas resection using the instrument can be performed if necessary.

Figure 6A:
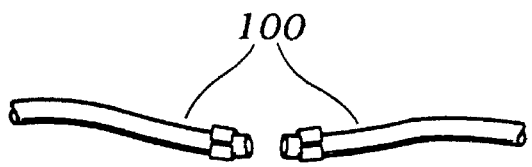
FIG. 6A–6E are views of the instrument of the present invention as used in a vasectomy reversal procedure.
Figure 6B:
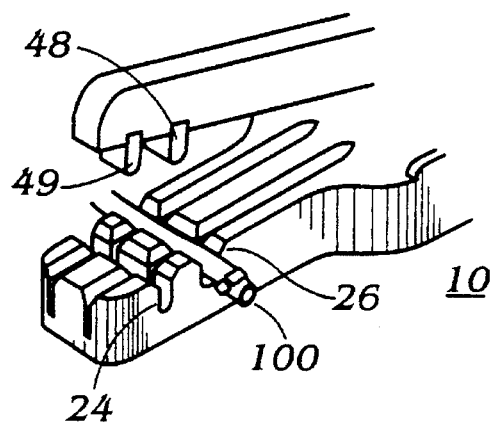
Figure 6C:
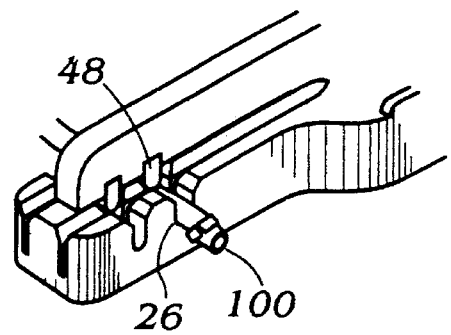
Figure 6D:
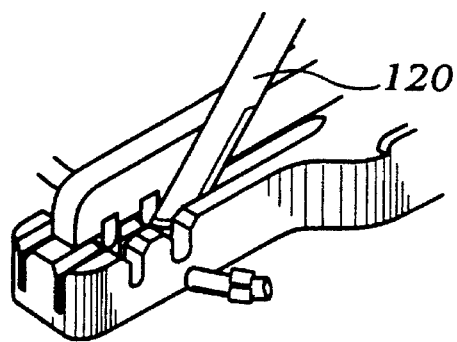
Figure 6E:
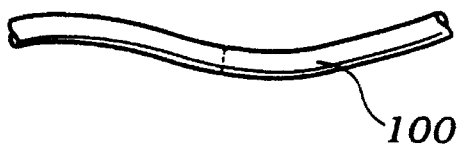

The proximal and distal flush, cut edges of the vas are then anastomosed according to standard surgical procedures, FIG. 6E.

While the invention has been particularly shown and described with reference to the preferred embodiments, it will be understood by those skilled in the art that various modifications and changes in form and detail may be made without departing from the scope and spirit of the invention. Accordingly, modifications such as those suggested above, but not limited thereto, are to be considered within the scope of the invention.

What is claimed is:

1. A surgical device for preparing body tissue for anastomosis by compressing body tissue and guiding a cutting blade comprising:

a base member having at least one holding groove for holding body tissue and at least one guide groove oriented substantially perpendicular to and intersecting said at least one holding groove for guiding a cutting blade;

a pressure-applying member cooperating with said base member, said pressure-applying member including a compliant finger located adjacent a distal end of said pressure applying member for atraumatically engaging and compressing a portion of said body tissue held within said at least one holding groove.

2. A surgical device according to claim 1 wherein said pressure-applying member comprises an arm mounting said compliant finger and pivotally mounted to said base member.

3. A surgical device according to claim 2 wherein said arm further comprises at least one finger grip for applying pressure to said arm.

4. A surgical device according to claim 2 further comprising means for urging said arm and said at least one compliant finger against said base member.

5. A surgical device according to claim 4 wherein said urging means comprises tension springs.

6. A surgical device according to claim 2 wherein the width of said arm and said compliant finger is less than the length of said at least one holding groove such that differential compression is applied along the length of body tissue.

7. A surgical device according to claim 2 wherein said at least one guide groove for guiding a cutting blade is positioned on said base member such that when said arm is seated against said base member said guiding groove is parallel and adjacent to said arm.

8. A surgical device according to claim 7 wherein said at least one guide groove for guiding a cutting blade comprises a pair of guide grooves positioned on said base member such that when said arm is seated against said base member said pair of guide grooves are parallel to and adjacent either side of said arm.

9. A surgical device according to claim 1 wherein said at least one holding groove for holding body tissue comprises two holding grooves of unequal size.

10. A surgical device for preparing body tissue for anastomosis by compressing body tissue and guiding a cutting blade comprising:

a base member having at least one holding means for holding body tissue and at least one groove for guiding a cutting blade substantially perpendicular to and intersecting said at least one holding means;

a pressure applying member cooperating with said base member, said pressure applying member including a compliant finger adapted to atraumatically compress a portion of said body tissue held within said at least one holding means, said compliant finger being provided with a curved tissue contacting surface dimensioned to fit within said at least one holding means for holding body tissue.

11. A surgical device for preparing body tissue for anastomosis by compressing body tissue and guiding a cutting blade comprising:

base means having means for holding body tissue and means for guiding a cutting blade, said guiding means disposed substantially perpendicular to and intersecting said means for holding body tissue and said means for holding body tissue includes at least one holding groove in said base means; and pressure applying means including a compliant finger to compress a portion of body tissue held by said at least one holding groove.

12. A surgical device according to claim 11 wherein said means for guiding a cutting blade comprises at least one guiding groove in said base means.

13. A surgical device according to claim 11 wherein said compliant finger is pivotally mounted to said base means.

14. A surgical device according to claim 11 wherein said compliant finger is configured and dimensioned to fit against said at least one holding groove.

15. A surgical device according to claim 11 further comprising tensioning means to urge said pressure applying means against said base means.

16. A method for preparing body tissue for subsequent anastomosis comprising:

providing the surgical device according to claim 11, inserting body tissue into the at least one holding groove, applying the pressure applying means, inserting a cutting blade into the guiding means, and transecting the body tissue with said cutting blade to form a first flush, cut end.

17. A method according to claim 16 wherein said body tissue is the vas deferens.

18. A method according to claim 16 wherein said guiding means include a first guiding groove and a second guiding groove, said step of inserting the cutting blade into the guiding means includes inserting the cutting blade into said first guiding groove, and after the step of transacting said tissue to form the first flush, cut end further including the steps of inserting the cutting blade into said second guiding groove and transacting said body tissue to form a second flush, cut end.

19. A method according to claim 18 further comprising anastomosing said first and second flush, cut ends.

20. A surgical device for compressing body tissue and guiding a cutting blade comprising:

a base member having at least one holding means for holding body tissue and first and second grooves for guiding a cutting blade substantially perpendicular to and intersecting said at least one holding means, said first and second grooves being of unequal size;

a pressure-applying member cooperating with said base member, said pressure-applying member having at least one projection adapted to atraumatically compress a portion of said body tissue held within said at least one holding means.

21. A surgical device for compressing body tissue and guiding a cutting blade comprising:

a base member having at least one holding means for holding body tissue and at least one groove oriented substantially perpendicular to and intersecting said at least one holding means for guiding a cutting blade;

a pressure-applying member cooperating with said base member, said pressure-applying member having at least one projection adapted to atraumatically compress a portion of said body tissue held within said at least one holding means, said pressure-applying member having a width less than the width of said at least one holding means such that differential compression is applied along the length of body tissue.

* * * * *